United States Patent
Royce et al.

(10) Patent No.: US 7,087,221 B2
(45) Date of Patent: Aug. 8, 2006

(54) SHAMPOO CONTAINING AN ALKYL ETHER

(75) Inventors: Douglas Allan Royce, Aurora, IN (US); Robert Lee Wells, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 596 days.

(21) Appl. No.: 10/301,945

(22) Filed: Nov. 22, 2002

(65) Prior Publication Data

US 2003/0143174 A1 Jul. 31, 2003

Related U.S. Application Data

(60) Provisional application No. 60/334,506, filed on Nov. 30, 2001.

(51) Int. Cl.
*A61Q 5/02* (2006.01)

(52) U.S. Cl. .................. 424/70.19; 424/70.31

(58) Field of Classification Search ............. None
See application file for complete search history.

(56) References Cited

U.S. PATENT DOCUMENTS

| | | |
|---|---|---|
| 5,876,705 A | 3/1999 | Uchiyama et al. |
| 5,980,877 A | 11/1999 | Baravetto et al. |
| 5,989,527 A | 11/1999 | Siegfried et al. |
| 6,174,522 B1 | 1/2001 | Baravetto et al. |
| 6,221,817 B1 | 4/2001 | Guskey et al. |
| 6,432,894 B1 | 8/2002 | Maurin et al. |
| 6,627,586 B1 | 9/2003 | Brooks |

| | | |
|---|---|---|
| 2003/0104957 A1 | 6/2003 | Loffler |

FOREIGN PATENT DOCUMENTS

| | | |
|---|---|---|
| EP | 0965322 A | 12/1999 |
| GB | 1360184 | 7/1974 |
| GB | 2242686 A | 10/1991 |
| JP | 2000336019 A | 5/1999 |
| WO | WO-93/08787 A2 | 5/1993 |
| WO | WO-94/20067 A1 | 9/1994 |
| WO | WO-95/01152 A1 | 1/1995 |
| WO | WO-97/26860 A1 | 7/1997 |
| WO | WO-99/13835 A1 | 3/1999 |
| WO | WO-99/38475 A1 | 8/1999 |
| WO | WO-01/17493 A1 | 3/2001 |

OTHER PUBLICATIONS

XP002232354, "Shower Gel Formulation", HAPPI Journal, Dec. 10, 2001, http://www.happi.com/special/1201form.htm.

XP002232355, "Dow Coming HMW2220 Non-Ionic Emulsion", http://wwwgalindberg.se/produktdata.htm.

*Primary Examiner*—Jyothsna Venkat
(74) *Attorney, Agent, or Firm*—Marianne Dressman; Brent M. Peebles; Tara M. Rosnell

(57) ABSTRACT

The compositions of the present invention relate to improved shampoo compositions having from about from about 5 to about 50 weight percent of a detersive surfactant, at least about 0.05 weight percent of a polyalkylene oxide alkyl ether selected from the group consisting of polyethylene glycol alkyl ethers, polypropylene glycol alkyl ethers, polyethylene glycol polypropylene glycol alkyl ethers, and combinations thereof, and at least about 20.0 weight percent of an aqueous carrier; wherein the polyalkylene oxide alkyl ether has an HLB of less than 10.

12 Claims, No Drawings

SHAMPOO CONTAINING AN ALKYL ETHER

CROSS REFERENCE TO RELATED APPLICATION

The application claims the benefit of U.S. Provisional application Ser. No. 60/334,506, filed on Nov. 30, 2001 in the names of Royce et al.

FIELD

The present invention relates to a hair cleansing shampoo containing an alkyl ether.

BACKGROUND

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair."

A variety of approaches have been developed to alleviate these after-shampoo problems. These approaches range from post-shampoo application of hair conditioners such as leave-on and rinse-off products, to hair conditioning shampoos which attempt to both cleanse and condition the hair from a single product.

In order to provide hair conditioning benefits in a cleansing shampoo base, a wide variety of conditioning actives have been proposed. However, many of these actives have the disadvantage of leaving the hair feeling soiled or coated and of interfering with the cleansing efficacy of the shampoo.

Coacervate formation in a shampoo composition is known to be advantageous for providing conditioning benefits to the hair. The use of cationic polymers to form coacervates are known in the art, such as in PCT publications WO93/08787 and WO95/01152. However, these shampoo compositions are good for delivering wet hair conditioning but are not capable of delivering satisfactory dry hair smooth feel.

Based on the foregoing, there is a need for a conditioning shampoo which can provide improved conditioning benefit for dry hair, while not interfering with the cleansing efficacy, nor providing negative feel to the hair when it is dried. Specifically, there is a need to provide long lasting moisturized feel, smooth feel, and manageability control to the hair when the hair is dried, yet not leave the hair feeling greasy, as well as to provide softness and ease of combing when the hair is wet.

None of the existing art provides all of the advantages and benefits of the present invention.

SUMMARY

The present invention is directed to a shampoo composition comprising:

a) from about 5 to about 50 weight percent of a detersive surfactant,
b) at least about 0.05 weight percent of a polyalkylene oxide alkyl ether selected from the group consisting of polyethylene glycol alkyl ethers, polypropylene glycol alkyl ethers, polyethylene glycol propylene glycol alkyl ethers, and combinations thereof, and
c) at least about 20.0 weight percent of an aqueous carrier;

wherein said polyalkylene oxide alkyl ether has an HLB of less than 10.

The present invention is further directed to a method of using the shampoo composition.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

The shampoo compositions of the present invention include detersive surfactant, a polyalkylene oxide alkyl ether and an aqueous carrier. Each of these essential components, as well as preferred or optional components, are described in detail hereinafter.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

All molecular weights as used herein are weight average molecular weights expressed as grams/mole, unless otherwise specified.

The term "charge density", as used herein, refers to the ratio of the number of positive charges on a monomeric unit of which a polymer is comprised to the molecular weight of said monomeric unit. The charge density multiplied by the polymer molecular weight determines the number of positively charged sites on a given polymer chain.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "insoluble" as used herein refers to any material that has a solubility in the composition at 25° C. of less than about 0.5%, preferably less than about 0.2%, even more preferably less than about 0.05% by weight.

The term "polymer" as used herein shall include materials whether made by polymerization of one type of monomer or made by two (i.e., copolymers) or more types of monomers.

The term "suitable for application to human hair" as used herein, means that the compositions or components thereof so described are suitable for use in contact with human hair and the scalp and skin without undue toxicity, incompatibility, instability, allergic response, and the like.

The term "water soluble" as used herein, means that the material is soluble in water in the present composition. In general, the material should be soluble at 25° C. at a concentration of 0.1% by weight of the water solvent, preferably at 1%, more preferably at 5%, most preferably at 15%.

All cited references are incorporated herein by reference in their entireties. Citation of any reference is not an admission regarding any determination as to its availability as prior art to the claimed invention.

A. Detersive Surfactant

The shampoo composition of the present invention includes a detersive surfactant. The detersive surfactant component is included to provide cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the shampoo composition herein include those which are known for use in hair care or other personal care cleansing compositions. The concentration of the anionic surfactant component in the shampoo composition should be sufficient to provide the desired cleaning and lather performance, and generally range from about 5% to about 50%, preferably from about 8% to about 30%, more preferably from about 10% to about 25%, even more preferably from about 12% to about 22%, by weight of the composition.

Preferred anionic surfactants suitable for use in the shampoo compositions are the alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic detersive surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 1 to about 5, more preferably about 2 to 3, molar proportions of ethylene oxide, and the resulting mixture of molecular species having, for example, an average of 3 moles of ethylene oxide per mole of alcohol, is sulfated and neutralized.

Specific non-limiting examples of alkyl ether sulfates which may be used in the shampoo compositions of the present invention include sodium and ammonium salts of coconut alkyl triethylene glycol ether sulfate, tallow alkyl triethylene glycol ether sulfate, tallow alkyl hexa-oxyethylene sulfate, and alkyldiethylene glycol ether sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic detersive surfactants are the water-soluble salts of organic, sulfuric acid reaction products conforming to the formula $[R^1—SO_3—M]$ where $R^1$ is a straight or branched chain, saturated, aliphatic hydrocarbon radical having from about 8 to about 24, preferably about 10 to about 18, carbon atoms; and M is a cation described hereinbefore. Non limiting examples of such detersive surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278, which descriptions are incorporated herein by reference.

Other anionic detersive surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880, which description is incorporated herein by reference.

Another class of anionic detersive surfactants suitable for use in the shampoo compositions are the beta-alkyloxy alkane sulfonates. These surfactants conform to the formula

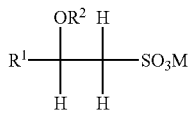

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Yet another class of anionic detersive surfactants suitable for use in the shampoo compositions are alkyl glyceryl ether sulfonate surfactants (also referred to herein as an "AGS" surfactant), derivatives thereof and salts thereof. AGS surfactants are derived from an alkyl glyceryl ether containing a sulfonate or sulfonate salt group. These compounds generally can be described as an alkyl monoether of glycerol that also contains a sulfonate group.

These AGS surfactants can be described as generally conforming to the following structures:

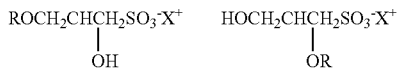

wherein R is a saturated or unsaturated straight chain, branched chain, or cyclic alkyl group having from about 10 to about 18 carbon atoms, preferably from about 11 to about 16 carbon atoms, and most preferably from about 12 to about 14 carbon atoms, and X is a cation selected from the group consisting of ammonium; mono-alkylsubstituted ammonium; di-alkylsubstituted ammonium; tri-alkylsubstituted ammonium; tetra-alkylsubstituted ammonium; alkali metal; alkaline metal; and mixtures thereof. More preferably, the alkyl radicals, R in the above formulas, are saturated and straight chain.

Preferred anionic detersive surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine laureth sulfate, monoethanolamine cocoyl sulfate, monoethanolamine lauryl sulfate, sodium tridecyl benzene sulfonate, sodium dodecyl benzene sulfonate, and combinations thereof.

Suitable amphoteric or zwitterionic detersive surfactants for use in the shampoo composition herein include those which are known for use in hair care or other personal care cleansing. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.), which descriptions are incorporated herein by reference.

Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, alkylaminoalkanoic acids, alkylaminoalkanoates and mixtures thereof. A particularly preferred amphoteric surfactant is cocaminopropionic acid.

Zwitterionic detersive surfactants suitable for use in the shampoo composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. A particularly preferred betaine is cocamidopropyl betaine.

The shampoo compositions of the present invention may further comprise additional surfactants for use in combination with the anionic detersive surfactant component described hereinbefore. Suitable optional surfactants include nonionic surfactants and cationic surfactants. Any such surfactant known in the art for use in hair or personal care products may be used, provided that the optional additional surfactant is also chemically and physically compatible with the essential components of the shampoo composition, or does not otherwise unduly impair product performance, aesthetics or stability. The concentration of the optional additional surfactants in the shampoo composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the shampoo compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which descriptions are incorporated herein by reference.

B. Polyalkylene Oxide Alkyl Ether

The composition of the present invention includes one or more polyalkylene oxide alkyl ethers. Preferably, the polyalkylene oxide alkyl ether is a polyethylene glycol alkyl ether, a polypropylene glycol alkyl ether, polyethylene glycol polypropylene glycol alkyl ethers, and combinations thereof.

Specific examples of useful polyalkylene oxide alkyl ethers include PPG-15 stearyl ether (available as ARLAMOL E™ from Uniqema), polyoxypropylene (9) decyl ether, polyoxypropylene (4) polyoxyethylene (6) cetyl ether, and polyoxyethylene (12) behenyl ether.

The polyalkylene oxide alkyl ethers of the present invention preferably have an average particle size greater than about 0.05 μm. More preferably, the polyalkylene oxide alkyl ethers have an average particle size greater than about 0.1 μm. Still more preferably, the polyalkylene oxide alkyl ethers have an average particle size greater than about 1 μm. In addition, the polyalkylene oxide alkyl ethers of the present invention preferably have an average particle size less than about 100 μm. More preferably, the polyalkylene oxide alkyl ethers have an average particle size less than about 75 μm. Still more preferably, the polyalkylene oxide alkyl ethers have an average particle size less than about 50 μm. In one embodiment, the polyalkylene oxide alkyl ether has an average particle size in the range of from 2 to 50 μm. In another embodiment, the polyalkylene oxide alkyl ether has an average particle size in the range of from 0.05 to 5 μm.

The polyalkylene oxide alkyl ethers of the present invention preferably have a HLB (Hydrophile-Lipophile Balance) of less than about 10. More preferably, the polyalkylene oxide alkyl ether has an HLB of less than 8.5. Still more preferably, the polyalkylene oxide alkyl ether has an HLB of less than 7. The HLB can be calculated by those skilled in the art using known methods. See *Emulsion Science* by P. Sherman pp. 140–153 (1968, Academic Press Inc.), herein incorporated by reference. For example, HLB values for polyhydric fatty acid esters can be calculated from analytical data $$HLB = 20(1 - S/A_v)$$

Where S is the saponification number of the ester, and $A_v$ is the acid value of the fatty acid radical. In certain cases, it is difficult to determine saponification numbers accurately, e.g., esters of tall oil, lanolin, rosin, etc., and for these a relationship based on a composition is used $$HLB = \frac{E + P}{5}$$

where E is the weight percentage of oxyethylene, and P is the weight percentage of polyhydric alcohol. When the only hydrophilic group present is ethylene oxide, and also for ethylene oxide derivatives, this reduces to $$HLB = \frac{E}{5}$$

As stated above, HLB is a common calculation known to those skilled in the art.

C. Aqueous Carrier

The compositions of the present invention include an aqueous carrier. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources containing mineral cations can also be used, depending on the desired characteristic of the product. Generally, the compositions of the present invention comprise from about 20% to about 95%, preferably from about 40% to about 92%, and more preferably from about 60% to abut 90% aqueous carrier.

The pH of the present composition is preferably from about 4 to about 9, more preferably from about 4.5 to about 7.5. Buffers and other pH adjusting agents can be included to achieve the desirable pH.

D. Additional Components

The shampoo compositions of the present invention may further comprise one or more optional components known for use in hair care or personal care products, provided that the optional components are physically and chemically compatible with the essential components described herein, or do not otherwise unduly impair product stability, aesthetics or performance. Individual concentrations of such optional components may range from about 0.001% to about 10% by weight of the shampoo composition.

Non-limiting examples of optional components for use in the shampoo composition include cationic polymers, particles, conditioning agents (hydrocarbon oils, fatty esters, silicones), anti dandruff agents, suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

Cationic Polymer

The composition of the present invention may optionally include a cationic deposition polymer of sufficiently high cationic charge density to effectively enhance deposition of the polyalkylene oxide alkyl ether component described herein. Suitable cationic polymers will have cationic charge densities of at least about 0.6 meq/gm, preferably at least about 0.9 meq/gm, more preferably at least about 1.2 meq/gm, but also preferably less than about 7 meq/gm, more preferably less than about 5 meq/gm, at the pH of intended use of the shampoo composition, which pH will generally range from about pH 3 to about pH 9, preferably between about pH 4 and about pH 8. The average molecular weight of such suitable cationic polymers will generally be between about 10,000 and 10 million, preferably between about 50,000 and about 5 million, more preferably between about 100,000 and about 3 million. The "cationic charge density" of a polymer, as that term is used herein, refers to the ratio of the number of positive charges on a monomeric unit of which the polymer is comprised to the molecular weight of said monomeric unit. The cationic charge density multiplied by the polymer molecular weight determines the number of positively charged sites on a given polymer chain.

The concentration of the cationic polymer in the shampoo composition ranges from about 0.05% to about 3%, preferably from about 0.075% to about 2.0%, more preferably from about 0.1% to about 1.0%, by weight of the shampoo composition. The weight ratio of cationic polymer to polyalkylene oxide alkyl ether in the shampoo compositions is from about 2:1 to about 1:30, preferably from about 1:1 to about 1:20, more preferably from about 1:2 to about 1:10.

The cationic polymer for use in the shampoo composition of the present invention contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the styling shampoo composition. Any anionic counterions can be use in association with the cationic polymers so long as the polymers remain soluble in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of such counterions include halides (e.g., chlorine, fluorine, bromine, iodine), sulfonate and methylsulfate.

The cationic nitrogen-containing moiety of the cationic polymer is generally present as a substituent on all, or more typically on some, of the monomer units thereof. Thus, the cationic polymer for use in the shampoo composition includes homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)), which description is incorporated herein by reference.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers preferably have from $C_1$ to $C_7$ alkyl groups, more preferably from $C_1$ to $C_3$ alkyl groups. Other suitable spacer monomers include vinyl esters, vinyl alcohol (made by hydrolysis of polyvinyl acetate), maleic anhydride, propylene glycol, and ethylene glycol.

Suitable cationic protonated amino and quaternary ammonium monomers, for inclusion in the cationic polymers of the shampoo composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$ alkyls.

Other suitable cationic polymers for use in the shampoo compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370 and FC 905); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively), such as those available under the MERQUAT tradename as Merquat 100 and Merquat 550 from Calgon Corp. (Pittsburgh, Pa., USA); amphoteric copolymers of acrylic acid including copolymers of acrylic acid and dimethyldiallylammonium chloride (referred to in the industry by CTFA as Polyquaternium 22) such as those available from Calgon Corp. under the Merquat tradename (e.g. Merquat 280 and 295), terpolymers of acrylic acid with dimethyldiallylammonium chloride and acrylamide (referred to in the industry by CTFA as Polyquaternium 39) such as those available from Calgon Corp. under the Merquat tradename (e.g. Merquat 3300 and 3331), and terpolymers of acrylic acid with methacrylamidopropyl trimethylammonium chloride and methacrylate (referred to in the industry by CTFA as Polyquaternium 47) available from Calgon Corp. under the Merquat tradename (e.g. Merquat 2001). Preferred cationic substituted monomers are the cationic substituted dialkylaminoalkyl acrylamides, dialkylaminoalkyl methacrylamides, and combinations thereof. These preferred monomers conform the to the formula

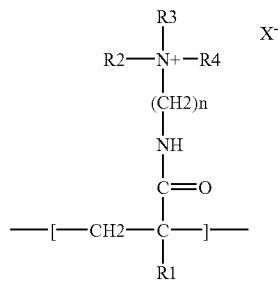

where $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc, Cranberry, N.J., U.S.A.

Other suitable cationic polymers for use in the shampoo composition include polysaccharide polymers, such as cationic cellulose derivatives and cationic starch derivatives. Suitable cationic polysaccharide polymers include those which conform to the formula:

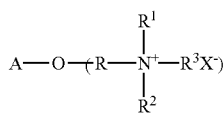

wherein A is an anhydroglucose residual group, such as a starch or cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion, as previously described. The degree of cationic substitution in these polysaccharide polymers is typically from about 0.01–1 cationic groups per anhydroglucose unit.

Preferred cationic cellulose polymers salts of hydroxyethyl cellulose reacted with trimethyl ammonium substituted epoxide, referred to in the industry (CTFA) as Polyquaternium 10 and available from Amerchol Corp. (Edison, N.J., USA) as Polymer JR30M with charge density of 1.25 meq/g and molecular weight of ~900,000, Polymer JR400 with charge density of 1.25 meq/g and molecular weight of ~400,000, and Polymer KG30M with a charge density of 1.9 and a molecular weight of ~1.25 million. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24.

Other suitable cationic polymers include cationic guar gum derivatives, such as guar hydroxypropyltrimonium chloride, specific examples of which include Jaguar C13 and C17, both commercially available from Rhone-Poulenc Incorporated. Other suitable cationic polymers include quaternary nitrogen-containing cellulose ethers, some examples of which are described in U.S. Pat. No. 3,962,418, which description is incorporated herein by reference herein. Other suitable cationic polymers include copolymers of etherified cellulose, guar and starch, some examples of which are described in U.S. Pat. No. 3,958,581, which description is incorporated herein by reference.

The cationic polymers herein are either soluble in the shampoo composition or are soluble in a complex coacervate phase in the shampoo composition formed by the cationic polymer and the anionic detersive surfactant component described hereinbefore. Complex coacervates of the cationic polymer can also be formed with other charged materials in the shampoo composition.

Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", Cosmetics & Toiletries, Vol. 106, April 1991, pp 49–54, C. J. van Oss, "Coacervation, Complex-Coacervation and Flocculation", J. Dispersion Science and Technology, Vol. 9 (5,6), 1988–89, pp 561–573, and D. J. Burgess, "Practical Analysis of Complex Coacervate Systems", J. of Colloid and Interface Science, Vol. 140, No. 1, November 1990, pp 227–238, which descriptions are incorporated herein by reference.

Complex coacervates are believed to readily deposit on the hair and to aid the deposition of other dispersed phases in the formulation, such as the polyalkylene oxide alkyl ethers mentioned above. It is believed to be particularly advantageous for the cationic polymer to be present in the shampoo composition in a coacervate phase, or to form a coacervate phase upon application or rinsing of the shampoo to or from the hair.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the shampoo composition.

In the compositions of the present invention, it is believed that the tendency for high charge density cationic polymers to form relatively large coacervates of sizes ranging from about 20 microns to about 500 microns which are capable of effectively binding or flocculating with the polyalkylene oxide alkyl ether and enhancing delivery to hair contributes to the superior deposition efficiency. Additionally, coacervates which have a cohesive character as evidenced by large, structured flocs which retain a substantial amount of the polyalkylene oxide alkyl ether component on dilution and resist deflocculation on exposure to shear enhance the deposition and retention of polyalkylene oxide alkyl ether polymers on hair.

Particles

The composition of the present invention optionally includes particles. The particles of the present invention preferably have a particle size of less than 300 µm. Typically, the particles will have a particle size from about 0.01 to about 80 µm, still more preferably from about 0.1 µm to about 70 µm, and even more preferably from about 1 µm to about 60 µm in diameter.

Typical particle levels are selected for the particular purpose of the composition. As example, where it is desired to deliver color benefits, pigment particles confering the desired hues can be incorporated. Where hair volume or style retention benefits are desired, particles capable of conferring friction can be used to reduce disruption and collapse of the hair style. Where conditioning or slip is desired, suitable platelet or spherical particles can be incorporated. Determination of the levels and particle types is within the skill of the artisan. Particles that are generally recognized as safe, and are listed in C.T.F.A. Cosmetic Ingredient Handbook, Sixth Ed., Cosmetic and Fragrance Assn., Inc., Washington D.C. (1995), incorporated herein by reference, can be used.

Conditioning Agents

Conditioning agents include any material which is used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The conditioning agents useful in the shampoo compositions of the present invention typically comprise a water insoluble, water dispersible, non-volatile, liquid that forms emulsified, liquid particles or are solubilized by the surfactant micelles, in the anionic detersive surfactant component (described above). Suitable conditioning agents for use in the shampoo composition are those conditioning agents characterized generally as silicones (e.g. silicone oils, cationic silicones, silicone gums, high refractive silicones, and silicon resins), organic conditioning oils (e.g. hydrocarbon oils, polyolefins, and fatty esters) or combinations thereof, or those conditioning agents which otherwise form liquid, dispersed, particles in the aqueous surfactant matrix herein. Such conditioning agents should be physically and chemically compatible with the essential components of the composition, and should not otherwise unduly impair product stability, aesthetics or performance.

The concentration of the conditioning agent in the shampoo composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the shampoo compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair (especially when high refractive index (e.g. above about 1:46) silicone conditioning agents are used (e.g. highly phenylated silicones).

The concentration of the silicone conditioning agent typically ranges from about 0.01% to about 10%, by weight of the composition, preferably from about 0.1% to about 8%, more preferably from about 0.1% to about 5%, most preferably from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609, which descriptions are incorporated herein by reference. The silicone conditioning agents for use in the shampoo compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, most preferably from about 100,000 to about 1,500,000 csk.

The dispersed, silicone conditioning agent particles typically have a number of average particle diameter ranging from about 0.01 µm to about 50 µm. For small particle application to hair, the number average particle diameters typically range from about 0.01 µm to about 4 µm, preferably from about 0.01 µm to about 2 µm, more preferably from about 0.01 µm to about 0.5 µm. For larger particle application to hair, the number average particle diameters typically range from about 4 µm to about 50 µm, preferably from about 6 µm to about 30 µm, more preferably from about 9 µm to about 20 µm, most preferably from about 12 µm to about 18 µm. Conditioning agents having an average particle size of less than about 5 µm may deposit more efficiently on the hair. It is believed that small size particles of conditioning agent are contained within the coacervate that is formed between the anionic surfactant component (described above) and the cationic polymer component (described below), upon dilution of the shampoo.

Background material on silicones including sections discussing silicone fluids, gums, and resins, as well as manufacture of silicones, are found in *Encyclopedia of Polymer Science and Engineering*, vol. 15, 2d ed., pp 204–308, John Wiley & Sons, Inc. (1989), incorporated herein by reference.

a. Silicone Oils

Silicone fluids include silicone oils, which are flowable silicone materials having a viscosity, as measured at 25° C., less than 1,000,000 cSt, preferably from about 5 cSt to about 1,000,000 cSt, more preferably from about 10 cSt to about 100,000 cSt. Suitable silicone oils for use in the shampoo compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (III):

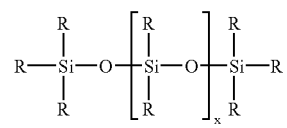

wherein R is aliphatic, preferably alkyl or alkenyl, or aryl, R can be substituted or unsubstituted, and x is an integer from 1 to about 8,000. Suitable unsubstituted R groups for use in the shampoo compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions herein, and are capable of being deposited on and conditioning the hair. The two R groups on the silicon atom of each monomeric silicone unit may represent the same or different groups. Preferably, the two R groups represent the same group.

Preferred alkyl and alkenyl substituents are $C_1$ to $C_5$ alkyls and alkenyls, more preferably from $C_1$ to $C_4$, most preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, most preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described above. The R substituents may also be substituted with other groups, such as halogens (e.g. chloride, fluoride, and bromide), halogenated aliphatic or aryl groups, hydroxy (e.g. hydroxy substituted aliphatic groups), and mixtures thereof. Suitable halogenated R groups could include, for example, tri-halogenated (preferably tri-fluoro) alkyl groups such as —$R^1 CF_3$, wherein $R^1$ is a $C_1$–$C_3$ alkyl. An example of such a polysiloxane includes, but is not limited to, polymethyl 3,3,3-trifluoropropylsiloxane.

Suitable R groups for use in the shampoo compositions of the present invention include, but are not limited to: methyl, ethyl, propyl, phenyl, methylphenyl and phenylmethyl. Specific non-limiting examples of preferred silicones include: polydimethyl siloxane, polydiethylsiloxane, and polymethylphenylsiloxane. Polydimethylsiloxane is especially preferred. Other suitable R groups include: methyl, methoxy, ethoxy, propoxy, and aryloxy. The three R groups on the end caps of the silicone may represent the same or different groups.

Non-volatile polyalkylsiloxane fluids that may be used include, for example, low molecular weight polydimethylsiloxanes. These siloxanes are available, for example, from the General Electric Company in their Viscasil R and SF 96 series, and from Dow Corning in their Dow Corning 200 series. Polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. Polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition described herein.

Alkylamino substituted silicones suitable for use in the shampoo compositions of the present invention include, but are not limited to, those which conform to the following general Formula (IV):

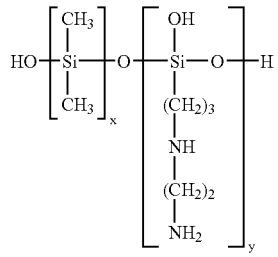

wherein x and y are integers. This polymer is also known as "amodimethicone."

b. Cationic Silicones

Cationic silicone fluids suitable for use in the shampoo compositions of the present invention include, but are not limited to, those which conform to the general formula (V):

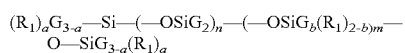

wherein G is hydrogen, phenyl, hydroxy, or $C_1$–$C_8$ alkyl, preferably methyl; a is 0 or an integer having a value from 1 to 3, preferably 0; b is 0 or 1, preferably 1; n is a number from 0 to 1,999, preferably from 49 to 149; m is an integer from 1 to 2,000, preferably from 1 to 10; the sum of n and m is a number from 1 to 2,000, preferably from 50 to 150; $R_1$ is a monovalent radical conforming to the general formula $C_qH_{2q}L$, wherein q is an integer having a value from 2 to 8 and L is selected from the following groups:

—$N(R_2)CH_2$—$CH_2$—$N(R_2)_2$
—$N(R_2)_2$
—$N(R_2)_3A^-$
—$N(R_2)CH_2$—$CH_2$—$NR_2H_2A^-$ wherein $R_2$ is hydrogen, phenyl, benzyl, or a saturated hydrocarbon radical, preferably an alkyl radical from about $C_1$ to about $C_{20}$, and $A^-$ is a halide ion.

An especially preferred cationic silicone corresponding to formula (V) is the polymer known as "trimethylsilylamodimethicone", which is shown below in formula (VI):

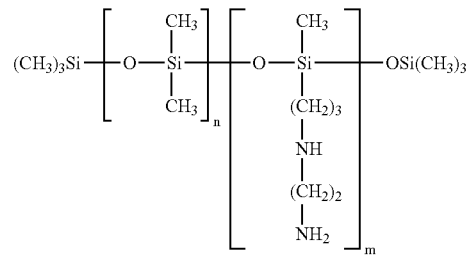

Other silicone cationic polymers which may be used in the shampoo compositions of the present invention are represented by the general formula (VII):

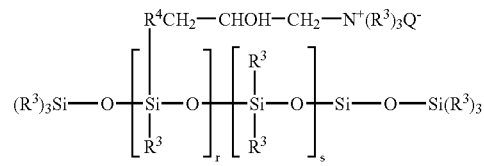

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

c. Silicone Gums

Other silicone fluids suitable for use in the shampoo compositions of the present invention are the insoluble silicone gums. These gums are polyorganosiloxane materials having a viscosity, as measured at 25° C., of greater than or equal to 1,000,000 cSt. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76, all of which are incorporated herein by reference. The silicone gums will typically have a weight molecular weight in excess of about 200,000, preferably from about 200,000 to about 1,000,000. Specific non-limiting examples of silicone gums for use in the shampoo compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

d. High Refractive Index Silicones

Other non-volatile, insoluble silicone fluid conditioning agents that are suitable for use in the shampoo compositions of the present invention are those known as "high refractive index silicones," having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

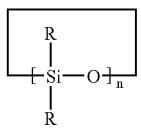

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described above. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted. Substituents include aliphatic substituents, and may also include alkoxy substituents, acyl substituents, ketones, halogens (e.g., Cl and Br), amines, and the like. Examples of aryl-containing groups include, but are not limited to, substituted and unsubstituted arenes, such as phenyl, and phenyl derivatives, such as phenyls with $C_1$–$C_5$ or alkenyl substituents. Specific non-limiting examples include: allylphenyl, methyl phenyl and ethyl phenyl, vinyl phenyls (e.g. styrenyl), and phenyl alkynes (e.g. phenyl $C_2$–$C_4$ alkynes). Heterocyclic aryl groups include, but are not limited to, substituents derived from furan, imidazole, pyrrole, pyridine, and the like. Examples of fused aryl ring substituents include, but are not limited to, napthalene, coumarin, and purine.

Generally, the high refractive index polysiloxane fluids will have a degree of aryl-containing substituents of at least about 15%, preferably at least about 20%, more preferably at least about 25%, even more preferably at least about 35%, most preferably at least about 50%. Typically, the degree of aryl substitution will be less than about 90%, more generally less than about 85%, preferably from about 55% to about 80%.

The high refractive index polysiloxane fluids are also characterized by relatively high surface tensions as a result of their aryl substitution. Generally, the polysiloxane fluids will have a surface tension of at least about 24 dynes/cm², typically at least about 27 dynes/cm². Surface tension, for purposes hereof, is measured by a de Nouy ring tensiometer according to Dow Corning Corporate Test Method CTM 0461 (Nov. 23, 1971). Changes in surface tension can be measured according to the above test method or according to ASTM Method D 1331.

Preferred high refractive index polysiloxane fluids have a combination of phenyl or phenyl derivative substituents (most preferably phenyl), with alkyl substituents, preferably $C_1$–$C_4$ alkyl (most preferably methyl), hydroxy, or $C_1$–$C_4$ alkylamino (especially —$R^1$NHR²NH2 wherein each $R^1$ and $R^2$ independently is a $C_1$–$C_3$ alkyl, alkenyl, and/or alkoxy).

High refractive index polysiloxanes are available from Dow Corning, Huls America, and General Electric.

When high refractive index silicones are used in the shampoo compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions. Generally, an amount of the spreading agent is used that is sufficient to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture may improve shine of the hair.

Also, the spreading agent will preferably reduce the surface tension by at least about 2 dynes/cm², preferably at least about 3 dynes/cm², even more preferably at least about 4 dynes/cm², most preferably at least about 5 dynes/cm².

The surface tension of the mixture of the polysiloxane fluid and the spreading agent, at the proportions present in the final product, is preferably less than or equal to about 30 dynes/cm², more preferably less than or equal to about 28 dynes/cm², most preferably less than or equal to about 25 dynes/cm². Typically, the surface tension will be in the range from about 15 dynes/cm² to about 30 dynes/cm², more typically from about 18 dynes/cm² to about 28 dynes/cm², and most generally from about 20 dynes/cm² to about 25 dynes/cm².

The weight ratio of the highly arylated polysiloxane fluid to the spreading agent will, in general, be from about 1000:1 to about 1:1, preferably from about 100:1 to about 2:1, more preferably from about 50:1 to about 2:1, most preferably from about 25:1 to about 2:1. When fluorinated surfactants are used, particularly high polysiloxane fluid to spreading agent ratios may be effective due to the efficiency of these surfactants. Thus, it is contemplated that ratios significantly above 1000:1 may be used.

Silicone fluids suitable for use in the shampoo compositions of the present invention are disclosed in U.S. Pat. No. 2,826,551, U.S. Pat. No. 3,964,500, U.S. Pat. No. 4,364,837, British Pat. No. 849,433, and *Silicon Compounds,* Petrarch Systems, Inc. (1984), all of which are incorporated herein by reference.

e. Silicone Resins

Silicone resins may be included in the silicone conditioning agent of the shampoo compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin. As is apparent to one of ordinary skill in the art, the degree of cross-linking that is required in order to result in a silicone resin will vary according to the specific silane units incorporated into the silicone resin. Generally, silicone materials which have a sufficient level of trifunctional and tetrafunctional siloxane monomer units (and hence, a sufficient level of cross-linking) such that they dry down to a rigid, or hard, film are considered to be silicone resins. The ratio of oxygen atoms to silicon atoms is indicative of the level of cross-linking in a particular silicone material. Silicone resins suitable for use in the shampoo compositions of the present invention generally have at least about 1:1 oxygen atoms per silicon atom. Preferably, the ratio of oxygen to silicon atoms is at least about 1.2:1.0. Silanes used in the manufacture of silicone resins include, but are not limited to: monomethyl-, dimethyl-, trimethyl-, monophenyl-, diphenyl-, methylphenyl-, monovinyl-, and methylvinyl-chlorosilanes, and tetra-chlorosilane, with the methyl-substituted silanes being most commonly utilized. Preferred resins are available from General Electric as GE SS4230 and GE SS4267. Commercially available silicone resins are generally supplied in a dissolved form in a low viscosity volatile or non-volatile silicone fluid. The silicone resins for use herein should be supplied and incorporated into the present compositions in such dissolved form, as will be readily apparent to one of ordinary skill in the art.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence. Typical alternate substituents include, but are not limited to, groups such as vinyl, phenyls, amines, hydroxyls, and the like. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin indicates higher levels of cross-linking. As discussed above, however, the overall level of cross-linking can also be indicated by the oxygen to silicon ratio.

Preferred silicone resins for use in the shampoo compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, most preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

2. Organic Conditioning Oils

The conditioning component of the shampoo compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones (described above).

It is believed that these organic conditioning oils provide the shampoo composition with improved conditioning performance when used in combination with the essential components of the composition, and in particular when used in combination with cationic polymers (described below). The conditioning oils may add shine and luster to the hair. Additionally, they may enhance dry combing and dry hair feel. Most or all of these organic conditioning oils are believed to be solubilized in the surfactant micelles of the shampoo composition. It is also believed that this solubilization into the surfactant micelles contributes to the improved hair conditioning performance of the shampoo compositions herein.

The organic conditioning oils suitable for use as the conditioning agent herein are preferably low viscosity, water insoluble, liquids selected from the hydrocarbon oils, polyolefins, fatty esters, and mixtures thereof. The viscosity, as measured at 40° C., of such organic conditioning oils is preferably from about 1 centipoise to about 200 centipoise, more preferably from about 1 centipoise to about 100 centipoise, most preferably from about 2 centipoise to about 50 centipoise.

a. Hydrocarbon Oils

Suitable organic conditioning oils for use as conditioning agents in the shampoo compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

b. Polyolefins

Organic conditioning oils for use in the shampoo compositions of the present invention can also include liquid polyolefins, more preferably liquid poly-α-olefins, most preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

c. Fatty Esters

Other suitable organic conditioning oils for use as the conditioning agent in the shampoo compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Suitable for use in the shampoo compositions of the present invention are alkyl and alkenyl esters of fatty acids having from about $C_{10}$ to about $C_{22}$ aliphatic chains, and alkyl and alkenyl fatty alcohol carboxylic acid esters having a $C_{10}$ to about $C_{22}$ alkyl and/or alkenyl alcohol-derived aliphatic chain, and mixtures thereof. Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the shampoo compositions of the present invention are mono-carboxylic acid esters of the general formula R'COOR, wherein R' and R are alkyl or alkenyl radicals, and the sum of carbon atoms in R' and R is at least 10, preferably at least 20. The mono-carboxylic acid ester need not necessarily contain at least one chain with at least 10 carbon atoms; rather the total number of aliphatic chain carbon atoms must be least 10. Specific non-limiting examples of mono-carboxylic acid esters include: isopropyl myristate, glycol stearate, and isopropyl laurate.

Still other fatty esters suitable for use in the shampoo compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, adipic acid, hexanoic acid, heptanoic acid, and octanoic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the shampoo compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the shampoo compositions of the present invention are glycerides, including, but not limited to, mono-, di-, and tri-glycerides, preferably di- and tri-glycerides, most preferably triglycerides. For use in the shampoo compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the shampoo compositions of the present invention are water insoluble synthetic fatty esters. Some preferred synthetic esters conform to the general Formula (IX):

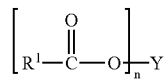

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

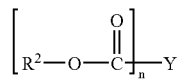

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

It is believed that the preferred synthetic esters provide improved wet hair feel when used in combination with the essential components of the shampoo compositions of the present invention, particularly when used in combination with the cationic polymer component (described below). These synthetic esters improve wet hair feel by reducing the slimy or excessively conditioned feel of wet hair that has been conditioned by a cationic polymer.

Specific non-limiting examples of suitable synthetic fatty esters for use in the shampoo compositions of the present invention include: P-43 ($C_8$–$C_{10}$ triester of trimethylolpropane), MCP-684 (tetraester of 3,3 diethanol-1,5 pentadiol), MCP 121 ($C_8$–$C_{10}$ diester of adipic acid), all of which are available from Mobil Chemical Company.

3. Other Conditioning Agents

Also suitable for use in the compositions herein are the conditioning agents described by the Procter & Gamble Company in U.S. Pat. Nos. 5,674,478 and 5,750,122, both of which are incorporated herein in their entirety by reference. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat.

No. 4,422,853 (L'Oreal), all of which descriptions are incorporated herein by reference.

Some other preferred silicone conditioning agents for use in the compositions of the present invention include: Abil® S 201 (dimethicone/sodium PG-propyldimethicone thiosulfate copolymer), available from Goldschmidt; DC Q2-8220 (trimethylsilyl amodimethicone) available from Dow Corning; DC 949 (amodimethicone, cetrimonium chloride, and Trideceth-12), available from Dow Corning; DC 749 (cyclomethicone and trimethylsiloxysilicate), available from Dow Corning; DC2502 (cetyl dimethicone), available from Dow Corning; BC97/004 and BC 99/088 (amino functionalized silicone microemulsions), available from Basildon Chemicals; GE SME253 and SM2115-D2 and SM2658 (amino functionalized silicone microemulsions), available from General Electric; siliconized meadowfoam seed oil, available from Croda; and those silicone conditioning agents described by GAF Corp. in U.S. Pat. No. 4,834,767 (quaternized amino lactam), by Biosil Technologies in U.S. Pat. No. 5,854,319 (reactive silicone emulsions containing amino acids), and by Dow Corning in U.S. Pat. No. 4,898,585 (polysiloxanes), all of which descriptions are incorporated herein by reference.

Anti-Dandruff Actives

The shampoo compositions of the present invention may also contain an anti-dandruff agent. Suitable, non-limiting examples of anti-dandruff particulates include: pyridinethione salts, selenium sulfide, particulate sulfur, and mixtures thereof. Preferred are pyridinethione salts. Such anti-dandruff particulate should be physically and chemically compatible with the essential components of the composition, and should not otherwise unduly impair product stability, aesthetics or performance.

1. Pyridinethione Salts

Pyridinethione anti-dandruff particulates, especially 1-hydroxy-2-pyridinethione salts, are highly preferred particulate anti-dandruff agents for use in shampoo compositions of the present invention. The concentration of pyridinethione anti-dandruff particulate typically ranges from about 0.1% to about 4%, by weight of the composition, preferably from about 0.1% to about 3%, most preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), most preferably 1-hydroxy-2-pyridinethione salts in platelet particle form, wherein the particles have an average size of up to about 20 µ, preferably up to about 5 µ, most preferably up to about 2.5 µ. Salts formed from other cations, such as sodium, may also be suitable. Pyridinethione anti-dandruff agents are described, for example, U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, all of which are incorporated herein by reference. It is contemplated that when ZPT is used as the anti-dandruff particulate in the shampoo compositions herein, that the growth or re-growth of hair may be stimulated or regulated, or both, or that hair loss may be reduced or inhibited, or that hair may appear thicker or fuller.

2. Selenium Sulfide

Selenium sulfide is a particulate anti-dandruff agent suitable for use in the shampoo compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), preferably less than 10 µm. Selenium sulfide compounds are described, for example, in U.S. Pat. No. 2,694,668; U.S. Pat. No. 3,152,046; U.S. Pat. No. 4,089,945; and U.S. Pat. No. 4,885,107, all of which descriptions are incorporated herein by reference.

3. Sulfur

Sulfur may also be used as a particulate anti-dandruff agent in the shampoo compositions of the present invention. Effective concentrations of the particulate sulfur are typically from about 1% to about 4%, by weight of the composition, preferably from about 2% to about 4%.

Humectant

The compositions of the present invention may contain a humectant. The humectants herein are selected from the group consisting of polyhydric alcohols, water soluble alkoxylated nonionic polymers, and mixtures thereof. The humectants, when used herein, are preferably used at levels by weight of the composition of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1, 2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glycosamine, cyclodextrin, and mixtures thereof.

Water soluble alkoxylated nonionic polymers useful herein include polyethylene glycols and polypropylene glycols having a molecular weight of up to abut 1000 such as those with CTFA names PEG-200, PEG-400, PEG-600, PEG-1000, and mixtures thereof.

Commercially available humectants herein include: glycerin with tradenames STAR™ and SUPEROL™ available from The Procter & Gamble Company, CRODEROL GA7000™ available from Croda Universal Ltd., PRECERIN™ series available from Unichema, and a same tradename as the chemical name available from NOF; propylene glyol with tradename LEXOL PG-865/855™ available from Inolex, 1,2-PROPYLENE GLYCOL USP available from BASF; sorbitol with tradenames LIPONIC™ series available from Lipo, SORBO™, ALEX™, A-625™, and A-641™ available from ICI, and UNISWEET 70™, UNISWEET CONC™ available from UPI; dipropylene glycol with the same tradename available from BASF; diglycerin with tradename DIGLYCEROL™ available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with the tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimaru Pharcos; sodium adenosine phosphate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; and polyethylene glycols with the tradename CARBOWAX series available from Union Carbide.

Suspending Agent

The shampoo compositions of the present invention may further comprise a suspending agent at concentrations effective for suspending the particle, or other water-insoluble material, in dispersed form in the shampoo compositions or for modifying the viscosity of the composition. Such concentrations range from about 0.1% to about 10%, preferably from about 0.3% to about 5.0%, by weight of the shampoo compositions.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose power, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Polyalkylene glycols having a molecular weight of more than about 1000 are useful herein. Useful are those having the following general formula:

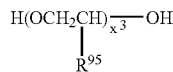

wherein $R^{95}$ is selected from the group consisting of H, methyl, and mixtures thereof. When $R^{95}$ is H, these materials are polymers of ethylene oxide, which are also known as polyethylene oxides, polyoxyethylenes, and polyethylene glycols. When $R^{95}$ is methyl, these materials are polymers of propylene oxide, which are also known as polypropylene oxides, polyoxypropylenes, and polypropylene glycols. When $R^{95}$ is methyl, it is also understood that various positional isomers of the resulting polymers can exist. In the above structure, x3 has an average value of from about 1500 to about 25,000, preferably from about 2500 to about 20,000, and more preferably from about 3500 to about 15,000. Other useful polymers include the polypropylene glycols and mixed polyethylene-polypropylene glycols, or polyoxyethylene-polyoxypropylene copolymer polymers. Polyethylene glycol polymers useful herein are PEG-2M wherein $R^{95}$ equals H and x3 has an average value of about 2,000 (PEG-2M is also known as Polyox WSR® N-10, which is available from Union Carbide and as PEG-2,000); PEG-5M wherein $R^{95}$ equals H and x3 has an average value of about 5,000 (PEG-5M is also known as Polyox WSR® N-35 and Polyox WSR® N-80, both available from Union Carbide and as PEG-5,000 and Polyethylene Glycol 300, 000); PEG-7M wherein $R^{95}$ equals H and x3 has an average value of about 7,000 (PEG-7M is also known as Polyox WSR® N-750 available from Union Carbide); PEG-9M wherein $R^{95}$ equals H and x3 has an average value of about 9,000 (PEG 9-M is also known as Polyox WSR® N-3333 available from Union Carbide); and PEG-14 M wherein $R^{95}$ equals H and x3 has an average value of about 14,000 (PEG-14M is also known as Polyox WSR® N-3000 available from Union Carbide).

Commercially available viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Hercules, ethylene oxide and/or propylene oxide based polymers with tradenames CARBOWAX PEGs, POLYOX WASRs, and UCON FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Long chain acyl derivatives, ethylene glycol esters of long chain carboxylic acids, long chain amine oxides, and alkanol amides of long chain carboxylic acids in addition to the preferred materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) C.sub.16, C.sub.18 and tallow amido benzoic acid species of this family, which are commercially available from Stepan Company (Northfield, Ill., USA).

Examples of suitable long chain amine oxides for use as suspending agents include alkyl (C.sub.16–C.sub.22) dimethyl amine oxides, e.g., stearyl dimethyl amine oxide). Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names: Acid Red 18, 26, 27,33, 51, 52, 87, 88, 92, 94, 95, Acid Yellow 1, 3, 11, 23, 36, 40, 73, Food Yellow 3, Food Green 3, Food blue 2, Food Red 1, 6, Acid Blue 5, 9, 74, Pigment Red 57-1, 53(Na), Basic Violet 10, Solvent Red 49, Acid orange 7, 20, 24, Acid Green 1, 3, 5, 25, Solvent Green 7, Acid Violet 9, 43; water insoluble components such as those having C. I. Names: Pigment Red 53(Ba), 49(Na), 49(Ca), 49(Ba), 49(Sr), 57, Solvent Red 23, 24, 43, 48, 72, 73, Solvent Orange 2, 7, Pigment Red 4, 24, 48, 63(Ca)3, 64, Vat Red 1, Vat blue 1, 6, Pigment Orange 1, 5, 13, Solvent Yellow 5, 6, 33, Pigment Yellow 1, 12, Solvent Green 3, Solvent Violet 13, Solvent Blue 63, Pigment Blue 15, titanium dioxides, chlorophyllin copper complex, ultramarines, aluminum powder, bentonite, calcium carbonate, barium sulfate, bismuthine, calcium sulfate, carbon black, bone black, chromic acid, cobalt blue, gold, ferric oxides, hydrated ferric oxide, ferric ferrocyanide, magnesium carbonate, manganous phosphate, silver, and zinc oxides.

The compositions of the present invention may also contain antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione.

The compositions of the present invention may also contain chelating agents such as: 2,2'-dipyridylamine; 1,10-phenanthroline {o-phenanthroline}; di-2-pyridyl ketone; 2,3-bis(2-pyridyl) pyrazine; 2,3-bis(2-pyridyl)-5,6-dihydropyrazine; 1,1'-carbonyldiimidazole; 2,4-bis(5,6-diphenyl-1,2,4-triazine-3-yl)pyridine; 2,4,6-tri(2-pyridyl)-1,3,5-triazine; 4,4'-dimethyl-2,2'dipyridyl; 2,2'-biquinoline; di-2-pyridyl glyoxal {2,2'-pyridil}; 2-(2-pyridyl)benzimidazole; 2,2'-bipyrazine; 3-(2-pyridyl)5,6-diphenyl-1,2,4-trazine; 3-(4-phenyl-2-pyridyl)-5-phenyl-1,2,4-triazine; 3-(4-phenyl-2-pyridyl)-5,6-diphenyl-1,2,4-triazine; 2,3,5,6-tetrakis-(2'-pyridyl)pyrazine; 2,6-pyridinedi-carboxylic acid; 2,4,5-trihydroxypyrimidine; phenyl 2-pyridyl ketoxime; 3-amino-5,6-dimethyl-1,2,4-triazine; 6-hydroxy-2-phenyl-3(2H)-pyridazinone; 2,4-pteridinediol {lumazine}; 2,2'-dipyridyl; and 2,3-dihydroxypyridine.

The compositions of the present invention may also contain viscosity modifiers, buffers, builders and perfumes.

METHOD OF USE

The shampoo compositions of the present invention are used in a conventional manner for cleansing hair or skin and providing enhanced deposition of polyalkylene oxide alkyl ethers and other benefits of the present invention. An effective amount of the composition for cleansing the hair or skin is applied to the hair or skin, that has preferably been wetted with water, and then rinsed off. Such effective amounts generally range from about 1 g to about 50 g, preferably from about 1 g to about 20 g. Application to the hair typically includes working the composition through the hair such that most or all of the hair is contacted with the composition. These steps can be repeated as many times as desired to achieve the desired cleansing and particle deposition benefits.

The polyalkylene oxide alkyl ethers of the present invention may also be useful in a hair conditioning composition, which may require no detersive surfactant or a lower level of detersive surfactant than that needed for a shampoo composition.

The following examples further describe and demonstrate the preferred embodiments within the scope of the present invention. The examples are given solely for the purpose of illustration, and are not to be construed as limitations of the present invention since many variations thereof are possible without departing from its scope.

EXAMPLES

The shampoo compositions illustrated in the following Examples illustrate specific embodiments of the shampoo compositions of the present invention, but are not intended to be limiting thereof. Other modifications can be undertaken by the skilled artisan without departing from the spirit and scope of this invention. These exemplified embodiments of the shampoo composition of the present invention provide enhanced deposition efficiency benefits of the particles.

The shampoo compositions illustrated in the following Examples are prepared by conventional formulation and mixing methods, an example of which is set forth hereinbelow. All exemplified amounts are listed as weight percents and exclude minor materials, such as diluents, preservatives, color solutions, imagery ingredients, botanicals, and so forth, unless otherwise specified.

The shampoo compositions of the present invention may be prepared using conventional formulation and mixing techniques. Where melting or dissolution of solid surfactants or wax components is required these can be added to a premix of the surfactants, or some portion of the surfactants, mixed and heated to melt the solid components, e.g., about 72° C. This mixture can then optionally be processed through a high shear mill and cooled, and then the remaining components are mixed in. The oil and silicone components can be added at any stage or emulsified to desired particle size in a premix and then added to the formulation. The compositions typically have a final viscosity of from about 2000 to about 20,000 cps. The viscosity of the composition can be adjusted by conventional techniques including addition of sodium chloride or ammonium xylenesulfonate as needed. The listed formulations, therefore, comprise the listed components and any minor materials associated with such components.

| EXAMPLE COMPOSITION | 1 | 2 | 3 | 4 | 5 | 6 | 7 | 8 | 9 | 10 |
|---|---|---|---|---|---|---|---|---|---|---|
| Ammonium Laureth-3 Sulfate | 10.00 | 10.00 | 10.00 | 10.00 | 10.00 | 10.00 | 10.00 | 10.00 | 10.00 | 10.00 |
| Ammonium Lauryl Sulfate | 6.00 | 2.00 | 2.00 | 2.00 | 2.00 | 2.30 | 2.00 | 2.00 | 2.00 | 2.00 |
| Cocamidopropyl Betaine FB | | 2.00 | 2.00 | 2.00 | 2.00 | | 2.00 | 2.00 | 2.00 | 2.00 |
| Sodium Lauraoamphoacetate | | 2.00 | 2.00 | 2.00 | 2.00 | | 2.00 | 2.00 | 2.00 | 2.00 |
| Cocaminoproprionic Acid | | | | | | 2.00 | | | | |
| Cetyl Alcohol | 0.90 | 0.60 | 0.60 | 0.60 | 0.60 | 0.60 | 0.60 | 0.60 | 0.60 | 0.60 |
| Cocamide MEA | 0.80 | 0.80 | 0.80 | 0.80 | 0.80 | 0.80 | 0.80 | 0.80 | 0.80 | 0.80 |
| Polyquaternium 10 (1) | 0.50 | 0.50 | 0.50 | 0.50 | 0.50 | 0.50 | 0.50 | | 0.50 | 0.50 |
| Guar hydroxypropyl trimonium chloride (5) | | | | | | | | 0.50 | | |
| Ethylene Glycol Distearate | 1.50 | 1.50 | 0.75 | 1.50 | 1.50 | 1.50 | 0.75 | 1.50 | 1.50 | 1.50 |
| Dimethicone (2) | 2.00 | | | | | | | | | |
| Dimethicone (3) | | 2.00 | 1.00 | | 2.00 | 2.00 | 2.00 | 2.00 | 2.00 | 1.00 |
| PPG 15 Stearyl Ether (4) | 2.00 | 2.00 | 2.00 | 2.00 | | 2.00 | 1.00 | 1.00 | 1.00 | 1.00 |
| Polyoxypropylene (4) polyoxyethylene (6) cetyl ether | | | | | 2.00 | | | | | |
| Perfume Solution | 0.70 | 0.70 | 0.70 | 0.70 | 0.70 | 0.70 | 0.70 | 0.70 | 0.70 | 0.70 |
| Sodium Citrate | 0.40 | 0.40 | 0.40 | 0.40 | 0.40 | 0.40 | 0.40 | 0.40 | 0.40 | 0.40 |
| Citric Acid | 0.04 | 0.40 | 0.40 | 0.40 | 0.40 | 0.04 | 0.04 | 0.04 | 0.04 | 0.04 |
| Water and Minors (QS to 100%) | | | | | | | | | | |

(1) Polymer KG30M available from Amerchol/Dow Chemical
(2) Viscasil 330M available from General Electric Silicones
(3) DC1664 available from Dow Corning Silicones
(4) Arlamol E available from Uniquema
(5) Cationic guar Jaguar C13 available from Aqualon It is understood that the examples and embodiments described herein are for illustrative purposes only and that various modifications or changes in light thereof will be suggested to one skilled in the art without departing from the scope of the present invention.

What is claimed is:

1. A shampoo composition comprising:
   a) from about 5 to about 50 weight percent of a detersive surfactant,
   b) at least about 0.05 weight percent of a polyalkylene oxide alkyl ether selected from the group consisting of PPG-15 stearyl ether, polyoxypropylene (9) decyl ether, polyoxypropylene (4) polyoxyethylene (6) cetyl ether, and polyoxyethylene (12) behenyl ether wherein said polyalkylene oxide alkyl ether has an average particle size of greater than about 0.05 μm and
   c) at least about 20.0 weight percent of an aqueous carrier; wherein said polyalkylene oxide alkyl ether has an HLB of less than 10.

2. The shampoo composition of claim 1 wherein said polyalkylene oxide alkyl ether is insoluble in said shampoo composition.

3. The shampoo composition of claim 1 wherein said polyalkylene oxide alkyl ether has an average particle size ranging from about 1 μm to about 100 μm.

4. The composition of claim 1 further comprising at least about 0.05 weight percent of a cationic polymer having a molecular weight of from about 10,000 to about 10,000,000 and a charge density from about 0.6 meq/gm to about 7.0 meq/gm.

5. The shampoo composition of claim 4 wherein said cationic polymer has a molecular weight of from about 50,000 to about 5,000,000.

6. The shampoo composition of claim 4 wherein said cationic polymer has a molecular weight of from about 100,000 to about 3,000,000.

7. The shampoo composition of claim 4 wherein said cationic polymer has a charge density of from about 0.9 meq/gm to about 5 meq/gm.

8. The shampoo composition of claim 4 wherein said cationic polymer has a charge density of from about 1.2 meq/gm to about 4.5 meq/gm.

9. The shampoo composition of claim 4 comprising from about 0.05 weight percent to about 3 weight percent of said cationic polymer.

10. The shampoo composition of claim 4 comprising from about 0.075 weight percent to about 2 weight percent of said cationic polymer.

11. The shampoo composition of claim 4 comprising from about 0.1 weight percent to about 1.0 weight percent of said cationic polymer.

12. A method of treating hair by administering a safe and effective amount of the composition according to claim 1.

* * * * *